United States Patent [19]

Stallcup et al.

[11] Patent Number: 4,722,842
[45] Date of Patent: Feb. 2, 1988

[54] GROWTH INHIBITORY FACTOR

[75] Inventors: Kathryn C. Stallcup, Boston, Mass.; Matthew F. Mescher, Del Mar, Calif.; Steven J. Burakoff, West Newton, Mass.

[73] Assignee: President and Fellows of Harvard College, Cambridge, Mass.

[21] Appl. No.: 786,833

[22] Filed: Oct. 11, 1985

[51] Int. Cl.$^4$ .................. A61K 35/12; A61K 35/413
[52] U.S. Cl. ........................................ 424/95; 424/106
[58] Field of Search .............................. 424/95, 106

[56] References Cited

PUBLICATIONS

Nakamura et al., 1984, J. Biol. Chem., vol. 259, pp. 8056–8058.
Grupp et al., 1985, J. Cell. Biol., vol. 101, pp. 380–385.
Mescher et al., 1982, Adv. Exp. Biol. Med., vol. 146, p. 41.
Whittenberger and Glaser, 1977, Proc. Natl. Acad. Sci., vol. 74, p. 2251.
Peterson and Lerch, 1983, J. Cell. Biol., vol. 97, p. 276.
Whittenberger et al., 1978, Proc. Natl. Acad. Sci., vol. 75, p. 5457.
Stallcup et al., 1984, J. Cell Biol., vol. 99, p. 1221.
Stallcup et al., 1984, J. Cell Biol., vol. 99, p. 1227.
Stallcup et al., 1984, Cell. Immun., vol. 89, p. 144.

Primary Examiner—J. R. Brown
Assistant Examiner—John W. Rollins, Jr.

[57] ABSTRACT

A purified growth inhibitory factor comprising a lipid-like compound derived from or substantially similar to the factor present in lymphocyte or liver cell plasma membranes is capable of inhibiting cytolytic T-lymphocyte killing response and mitogen-induced B cell, T cell, or lymphoid tumor cell proliferation.

12 Claims, No Drawings

GROWTH INHIBITORY FACTOR

BACKGROUND OF THE INVENTION

This invention relates to the inhibition of cell growth.

Cell-cell interactions play a central role in initiation of many immune responses. Lymphocyte recognition of surface components on adjacent cells leads, in some cases, to proliferation and/or differentiation of the lymphocyte. Plasma membranes isolated from cells, or artificial membranes (liposomes), which bear the relevant isolated membrane factors, can trigger responses that are normally initiated by cell-cell contact (Mescher et al. 1982 Adv. Exp. Biol. Med. 146:41). Evidence supporting the importance of cell contact in regulatory events includes the finding that isolated plasma membranes inhibit the growth of 3T3 cells in vitro (Whittenberger and Glaser, 1977, Proc. Natl. Acad. Sci. 74:2251), and that such inhibition appeared to be cell specific (Peterson and Lerch, 1983, J. Cell Biol. 97:276); and probably caused by a membrane protein (Wittenberger et al. 1978 Proc. Natl. Acad. Sci. 75:5457).

SUMMARY OF THE INVENTION

The invention features a growth inhibitory factor comprising a lipid-like compound derived from or substantially similar to a compound present in lymphocyte or liver cell plasma membranes. The factor inhibits the cytolytic T-lymphocyte killing response, mitogen-induced B cell or T cell proliferation, and tumor cell growth in vitro. The growth inhibitory factor appears to inhibit DNA synthesis.

The growth inhibitory factor can be enriched by passage over a monoclonal antibody column containing antibodies to H-2 antigens and further enriched by gel filtration, which separates the factor from H-2 antigens. On the gel filtration column the inhibitory factor elutes with an apparent molecular weight of 30,000–40,000 daltons; although its real molecular weight is probably less than 1,000 daltons. Other methods for enriching the lipid-like growth inhibitory factor include organic solvent extraction of whole lymphoid cells or of isolated plasma membranes, preferably with a mixture of butanol and pyridinium acetate. In another embodiment the factor may be extracted by the solubilization of membranes or cells with deoxycholate followed by centrifugation to remove insoluble fractions. More refined purification of the lipid-like component may be achieved by passage of organic solvent extracts through a silicic acid column or over an HPLC column.

Other features and advantages of the invention will be apparent from the following descriptions of the preferred embodiments and from the claims.

DESCRIPTION OF THE PREFERRED EMBODIMENTS

Structure

Mice, Cell Lines, and Tissue Culture

Mouse strains used for in vitro assays included (BALB/c×DBA/2)F$_1$(CD2F$_1$) from Cumberland Farms, Clinton, TN; and AKR, BALB/c, C57BL/6, and (AKR×DBA/2)F$_1$(AKD2F$_1$), (C57BL/6×A/J)F$_1$(B6AF$_1$) from the Jackson Laboratory (Bar Harbor, ME).

Tumor cell lines used for in vitro assays include P815, and mastocytoma, RDM-4, a lymphoma, the thymoma lines, EL4 and BW1547, and RIE/TL8X.1, and a mutant lymphoma line (Hyman and Trowbridge, 1977, Cold Spring Harbor Symp. Quant. Biol., 41:407). P815, RDM-4 and EL4 were routinely maintained by intraperitoneal passage in CD2F$_1$, AKR, and C57BL/6, respectively. BW5147 and R1E/TL8X.1 were maintained in vitro in Dulbecco's modified Eagle's medium. Tumor cells were grown in vitro at 37° using RPMI 1640 (Gibco) supplemented with 10% fetal calf serum, 2 mM glutamine, 50 units/ml penicillin, and 50 mg/ml streptomycin, in a 5% $CO_2$ atmosphere.

Macrophage hybridoma lines were produced by fusing spleenic adherent cells from CKB mice (H-$2^k$) with a drug-marked macrophage-like line, P388D$_1$(H-$2^d$). The production and properties of these hybridomas have been described by Eugeta et al. (1985, J. Immunology 134:772) and Liu et al. (1985, Cell Immunol. 94:49) and are therefore well known in the art.

Liver cells were obtained from C57 BL/6 mice (Jackson Labs, Bar Harbor, ME).

Membranes

Crude membranes were isolated according to the method of Lemonnier et al. (1978, J. Immunol. 120:1114). Briefly the cells were lysed by nitrogen cavitation, the nuclei removed by low speed centrifugation and crude membranes isolated by centrifugation of the remaining lysate. Plasma membranes were separated by sucrose density gradient centrification.

Lipid-Like Factor (Inhibitor)

The lipid-like factor of the invention is a growth inhibitor as measured by CTL and LPS assays (see below). The factor was enriched by a variety of methods including the isolation of plasma membranes from the above cell lines and subsequent treatment of these membranes, or of the original cells, with organic solvents, whereby the lipid components were extracted. In some experiments the cells or membranes were solubilized in deoxycholate followed in some instances by gel filtration on Biogel columns. Alternatively, cells or membranes were solubilized in Triton X-100 followed by affinity chromatography on columns of monoclonal anti H-2 antibodies coupled to Sepharose 4B. More refined purification methods used were silicic acid chromatography and HPLC (see below). The lipid-like factor appears to inhibit cellular responses by inhibiting DNA synthesis.

Methods

Assay of Growth Inhibitory Activity (a) Cytotoxic T lymphocytes (CTL)

Methods for the in vitro generation and assay of allogenic CTL have been described in detail (Lemonnier ibid., and Burakoff et al. Proc. Natl. Acad. Sci. 73:625). Briefly, mice such as C57BL/6 (H-$2^b$) or CD2F$_1$(H-$2^d$) were primed intraperitoneally with cells such as P815 (H-$2^d$) or RDM-4 (H-$2^k$) respectively. Four to six weeks later, spleen cells were removed, placed in culture, and the appropriate radiated tumor cells, membranes, or purified lipid-like factor added. Lytic activity was assayed five days later using a standard $^{51}$Cr-release assay (Burakoff et al. ibid.). The presence of the lipid-like factor inhibited this activity.

(b) Lipopolysaccaride (LPS) induced mitogenic response.

Spleen cells from normal mice were cultured either in the presence or absence of LPS. The LPS assay was performed as described in Stallcup et al. I (1984, J. Cell Biol. 99:1221), as well known in the art. Briefly LPS was added to cells in media and after two days of culture at 37° one microCurie of tritiated thymidine (New England Nuclear) was added to each sample for a six hour incubation period. The amount of thymidine incorporated was calculated by standard procedures. This incorporation was reduced when the lipid-like factor was present in the assay.

(c) Tumor cell growth.

In vitro growth of tumor cells was performed as described by Stallcup et al. II (1984, J. Cell. Biol. 99:1227). Briefly cells were grown in Limbro wells (Limbro Chem-Co., Hamden, CT) in medium at 37° C. in a $CO_2$, atmosphere. The inhibitory activity of the lipid-like factor, in the tumor cell growth assays could be reversed by washing the test cells with medium up to 48 hours after the start of the test.

Solubilization and Reconstitution of Membranes

Isolated crude membranes were solubilized with deoxycholate as described by Stallcup et al. (ibid.). Briefly the cytoplasmic membranes were solubilized with deoxycholate and the detergent soluble and insoluble fraction separated by centrifugation at $100,000 \times g$ for 45 minutes. The detergent soluble and insoluble materials were reconstituted by dialysis against Tris buffered saline, (TBS) containing calcium chloride.

Affinity Chromotography

H-2 antigens were affinity purified using monoclonal antibodies covalently coupled to Sepharose 4B (Pharmacia Fine Chemicals) as described by Stallcup et al. (1984, J. Cell Biol. 99:1227). Briefly cells or membranes were solubilized by suspension in Triton X-100. The lysate was centrifuged to remove insoluble material, and passed over the affinity column. Bound antigen, containing the inhibitory growth factor, was eluted with deoxycholate in TBS.

Liposome Formation

Lipids for the formation of liposomes were obtained by chloroform-methanol extraction of P815 cells (Herrmann and Mescher 1981, Proc., Natl. Acad. Sci. 78:2488). Liposomes were prepared as described by Stallcup et al. (1984, J. Biol. 99:1227) and Stallcup et al (1984, Cell. Immun. 89:144). Briefly the material to be incorporated into liposomes was mixed with crude lipids, prepared from the above membranes, or alternatively from dimyristoyl phosphatidylcholine (Sigma Chemical Company, St. Louis, MO), and the mixture was then dialyzed against TBS for 24 hours. After further dialysis against TBS containing calcium chloride, the liposomes were concentrated by centrifugation for 90 minutes at $100,000 \times g$.

Organic Extraction

Organic solvent extractions were performed using butanol and pyridinium acetate as described by Stallcup et al. (J. Biol. 99:1227 1984). Whole cells, membranes, or purified H-2 antigens were extracted and the organic phase removed and dried under a nitrogen stream. The resulting lipid film can be sonicated into aqueous buffers or medium for use in bioassays, or can be dissolved in organic solvents.

Thin Layer Chromatography

Thin layer chromotography was performed on silica gel G plates (Anal. Tech. Newark, DE) using a solvent system of chloroform-methanol-water (60:35:8). Samples were applied directly to the plates in organic solvents or aqueous buffer and dried. After developing and drying the plates lipids were visualized by exposure to iodine vapor.

Gel Filtration

Gel filtration was carried out on Bio-gel A (BioRad Laboratories, Richmond, CA) equilibrated with 0.25% deoxycholate and TBS, as described by Stallcup et al. (1984 J Cell Biol. 99:1227).

Silicic Acid Column Chromatography

A sample was applied to a column of Biosil A (100-200 mesh, BioRad) that had been thoroughly washed with loading solvent. Two elution systems were used. The first employed different ratios of chloroform and methanol (95:5, 85:15, 50:50 and 0:100). The second type of elution employed sequential steps of chloroform, acetone, and methanol (Kates M., 1972, Techniques of Lipidology: Isolation analysis and identification of lipids. New York, American Elsevier Pub. Co., Inc.). In each of these systems, neutral lipids eluted in the presence of high chloroform concentrations, more polar lipids eluted in the presence of methanol, and acetone eluted certain glycolipids. Inhibitory activity eluted when solvents with a high methanol content (greater than 50%) were used, and could be recovered quantatively from the column.

High Performance Liquid Chromatography (HPLC)

The sample was loaded onto a Lichrospher Si100 column (Applied Science) and eluted with a mixture of acetonitrile, methanol and sulfuric acid (100:4:0.1). Fractions were removed at intervals.

Isolation of Lipid-Like Factor (Inhibitor)

The lipid-like inhibitory factor was isolated in either a crude or a highly enriched form. Crude membrane preparations from any of the above described cells or from liver cells contain the lipid-like factor which can be detected by its inhibitory activity, measured as the inhibition in vitro of the CTL or LPS responses. Such activity is resistant to heating at 100° C. for 10 minutes and to treatment with proteases. The following examples demonstrate purification of the inhibitory factor.

EXAMPLE 1

Crude membranes from P815 cells, from RDM-4 tumor cells, and from normal C57BL/6 spleen cells were prepared as described above. These crude membrane preparations were further fractionated by density gradient centrifugation to give fractions enriched in plasma membrane or in endoplasmic reticulum. Mearsurement of marker enzymes (Lemonnier et al. ibid.) indicated that the plasma membrane fractions were enriched 2-5 fold. Such fractionation gave a 2.5 fold enrichment of inhibitory activity (i.e. lipid-like factor) compared to the crude membranes; 80 mg/ml of the plasma membrane now giving 50% inhibition compared to the endoplasmic reticulum fraction where 200 mg/ml was required for such inhibition. Solubilization and reconstitution of these membranes with deoxycholate did not remove the inhibitory activity.

EXAMPLE 2

H-2 antigens were affinity purified as described above, examined by polyacrylamide gel electrophoresis and determined to be in relatively pure form. Minor contaminents were undetectable in most preparations. These antigens were incorporated into liposomes as described above and their activity in inhibiting the CTL response the LPS response, and the growth of several in vitro turmor cell lines observed. When the antigen concentration was greater than 1 mg/ml, inhibitory acitivity was detected. These responses were observed with antigens isolated from cell lines EL-4, CH-1, and RDM-4, and with the purified H-2$K^k$, H-2$D^k$, or H-2$K^dD^d$ glycoproteins. Thus the inhibitory activity was not genetically restricted to either haplotype or strain. The lipid-like factor was also isolated from the mutant cell line RIE/TL8X-1, which does not express H-2 antigens on the cell surface. Thus the factor is not one of the H-2 antigens, but copurifies with them.

EXAMPLE 3

The lipid-like factor from P815 membranes was isolated by solubilizing the crude membranes in 0.5% deoxycholate in TBS and centrifuging the lysate to remove insoluble material, as described above. Gel fitration was performed as described above and the inhibitor was recovered in a peak eluting, with 0.25% deoxycholate in TBS, at the same position as that found for the inhibitor present in H-2 antigen preparations. The H-2 antigens were eluted at a position corresponding to an apparent molecular weight of approximately 110,000 daltons. The inhibitory activity appears to elute as an aggregate of many lipid and detergent molecules, with an apparent molecular weight of 35,000 daltons. It should be noted that gel filtration columns are designed to size water-soluble proteins, and thus are not able to provide accurate size information for membrane components (either protein or lipid) which, for most lipids, is less than 1,000 daltons.

EXAMPLE 4

Whole cells, membranes, or partially purified antigens were dialyzed and then extracted with 2:1 butanol/pyridinium acetate, pH 4.2, as described above. The inhibitor was present in the organic phase and could be quantitatively recovered. Similarly, extractions using chloroform, methanol and water (2:1:0.3) recovered the inhibitory factor in the organic phase. The inhibitor did not have to be dialyzed into liposomes but was active when sonicated directly into medium. Thin layer chromatography of the purified lipid preparation was performed as described above and revealed approximately 10 lipid-like molecules from whole membranes, and approximately three lipid-like molecules from purified antigen preparations.

EXAMPLE 5

Two groups of cloned macrophage hybridoma lines have been described (Liu et al. ibid.). One group inhibits in vitro proliferation of B and T lymphocytes and lymphoid tumor cells, whilst the other group has little or no inhibitory activity. The first group includes the hybridoma clones 58, 63 and 64, whilst the non-inhibitory group includes the hybridoma clones 13,59 and 67 as well as the parental cell line P388$D_1$. The lipid-like inhibitory factor was extracted from these groups as described in the examples above. The level of inhibitor in the inhibitory group was substantially greater (approximately 10 fold) than that in the non-inhibitory group. Thus, clones such as those in the inhibitory group provide a more concentrated source of the lipid-like factor than normal cells.

EXAMPLE 6

A crude membrane fraction from P815 cells was extracted with organic solvents as described in Example 4 above. The dried lipid film was brought up in the appropriate solvent and applied to a Biosil column. The inhibitory factor eluted from the silicic acid by solvents with a high methanol content (greater than 50%), was dried under nitrogen and then sonicated into tissue culture medium. The inhibitory activity was found in the fraction containing phospholipids.

EXAMPLE 7

An organic solvent extract of crude membranes was chromatagraphed on a BioSil column as described in Example 6 above and the methanol eluate dried, brought up in chloroform, filtered and loaded onto an HPLC column. Peaks corresponding to phosphatidyl ethanolamine (8 minutes), phosphatidyl choline (11 minutes) and the inhibitory activity (13 minutes) were recovered. The inhibitor was separated from the bulk of material absorbing at an optical density of 205 nm.

USES

The lipid-like inhibitor is useful for the study of the action of growth factors such as IL2. It can also be used to study the regulation of DNA synthesis, of which it appears to be an inhibitor. It inhibits cell proliferation in lymphocytes and in lymphoid tumor cell lines as well as in other types of cells. The inhibitory effect of the growth inhibitory factor of the present invention is reversible, cell proliferation being resumed when the factor is removed. Since inhibition caused by the factor is reversible, the factor could be used to synchronize cell growth, and it may also be possible to induce the differentiation of various cells by treatment with the factor. It may be possible to couple this inhibitor to tumor specific antibodies, similar to the way the ricin "A" chain has been coupled (Krolick, K. et al. 1980, Proc. Natl. Acad. Sci. (USA) 77:5419.), and thereby produce a molecule capable of specifically inhibiting growth of particular cells. Further the encapsulation of the lipid-like factor into a liposome could allow the selective disturbance, in vivo, of more rapidly growing cells, such as tumor cells.

Other embodiments are within the following claims.

We claim:

1. A composition enriched for a growth inhibitory factor comprising a lipid-like compound which is obtainable by extraction from lymphocyte or liver cell plasma membrane, said composition being characterized in that said inhibitory factor inhibits the cytolytic T-lymphocyte killing response.

2. The composition of claim 1 further characterized in that said inhibitory factor inhibits DNA synthesis.

3. The composition of claim 1 or 2 further characterized in that said inhibitory factor has an apparent molecular weight, on a gel filtration column, eluted with deoxycholate, of 30,000–40,000 daltons.

4. The composition of claim 1 further characterized in that said inhibitory factor inhibits tumor cell growth in vitro.

5. The composition of claim 1 further characterized in that said inhibitory factor inhibits mitogen-induced B cell and T cell proliferation.

6. A method of purifying a lipid-like growth factor as claimed in claim 1 which method comprises
   subjecting a lymphocyte or liver cell to lysis with deoxycholate,
   separating plasma cell membrane from said lystate by centrifugation, extracting said membrane with an organic solvent, and drying said extract.

7. A method of purifying a lipid-like growth inhibitory factor characterized by the ability to inhibit the cytolytic T-lymphocyte killing response, said method comprising organic solvent extraction of a lymphoid or liver cell.

8. The method of claim 7 wherein said organic solvent extraction comprises addition of 2:1 n-butanol/6M pyridinium acetate pH 4–6 to said cell, followed by separation of the solvent phase and removing said organic solvent therefrom.

9. The method of claim 8 wherein, prior to said extraction, said cell is subjected to fractionation by centrifugation in a sucrose step gradient.

10. The method of claims 7 or 8 wherein said method further comprises purifying said growth inhibitory factor by passage through a silicic acid column.

11. The method of claim 10 wherein said method further comprises the purification of said growth factor by passage through an HPLC column.

12. An essentially purified lipid-like growth inhibitory factor obtainable by solvent extraction from lymphocyte or liver cell plasma membranes, said factor having the following characteristics:
    (a) it inhibits the cytolytic T-lymphocyte killing response;
    (b) it inhibits DNA synthesis;
    (c) it inhibits tumor cell growth in vitro; and
    (d) it inhibits mitogen-induced B cell and T cell proliferation.

* * * * *

UNITED STATES PATENT AND TRADEMARK OFFICE
CERTIFICATE OF CORRECTION

PATENT NO. : 4,722,842

DATED : February 2, 1988

INVENTOR(S) : Kathryn C. Stallcup et al.

It is certified that error appears in the above-identified patent and that said Letters Patent are hereby corrected as shown below:

Col. 6, claim 1, line 2, after "compound", insert
--substantially similar or identical to a compound--.

Signed and Sealed this

Fifth Day of July, 1988

Attest:

Attesting Officer

DONALD J. QUIGG

Commissioner of Patents and Trademarks